US008642825B2

(12) United States Patent
Kustov et al.

(10) Patent No.: US 8,642,825 B2
(45) Date of Patent: Feb. 4, 2014

(54) MEMBRANE-SUPPORTED CATALYSTS AND THE PROCESS OF OXIDATIVE DEHYDROGENATION OF ETHANE USING THE SAME

(75) Inventors: Leonid Modestovich Kustov, Moscow (RU); Aleksey Victorovich Kucherov, Moscow (RU); Elena Dmitrievna Finashina, Moscow (RU); Vasily Simanzhenkov, Calgary (CA); Andrzej Krzywicki, Calgary (CA)

(73) Assignee: Nova Chemicals (International) S.A., Fribourg (CH)

( * ) Notice: Subject to any disclaimer, the term of this patent is extended or adjusted under 35 U.S.C. 154(b) by 0 days.

(21) Appl. No.: 13/614,754

(22) Filed: Sep. 13, 2012

(65) Prior Publication Data

US 2013/0072737 A1      Mar. 21, 2013

(30) Foreign Application Priority Data

Sep. 19, 2011   (CA) .................................... 2752409

(51) Int. Cl.
*C07C 5/327* (2006.01)
*C07C 5/373* (2006.01)
*C07C 5/333* (2006.01)

(52) U.S. Cl.
USPC ............ 585/658; 585/661; 585/662; 585/663

(58) Field of Classification Search
USPC ........................................................ 585/658
See application file for complete search history.

(56) References Cited

U.S. PATENT DOCUMENTS

| 4,250,346 | A | 2/1981 | Young et al. |
| 4,450,313 | A | 5/1984 | Eastman et al. |
| 4,524,236 | A | 6/1985 | McCain |
| 4,596,787 | A | 6/1986 | Manyik et al. |
| 4,899,003 | A | 2/1990 | Manyik et al. |
| 6,518,476 | B1 * | 2/2003 | Culp et al. ................... 585/655 |
| 6,521,808 | B1 | 2/2003 | Ozkan et al. |
| 6,566,573 | B1 | 5/2003 | Bharadwaj et al. |
| 6,624,116 | B1 | 9/2003 | Bharadwaj et al. |
| 6,730,808 | B2 | 5/2004 | Bitterlich et al. |
| 6,891,075 | B2 | 5/2005 | Liu |
| 7,319,179 | B2 * | 1/2008 | Lopez Nieto et al. ........ 585/658 |
| 2007/0151857 | A1 * | 7/2007 | Farrusseng et al. ........... 204/639 |

FOREIGN PATENT DOCUMENTS

| WO | WO 2005018804 A1 | 3/2005 |
| WO | WO 2006/024785 A1 | 3/2006 |
| WO | WO 2006130288 A1 | 12/2006 |

OTHER PUBLICATIONS

Acres, G.J.K, A.J. Bird, J.W. Jenkins and F. King, The Design and Preparation of Supported Catalysts, RSC Publishing, Copyright Year 1981, Catalysis vol. 4.*
Ivars, et al; Selective oxidation of short-chain alkanes over hydrothermally prepared MoVTeNbO catalysts; Topics in Catalysis; vol. 38; Nos. 1-3; Jul. 2006; pp. 59-67.
Dalmon et al; Oxidation in catalytic membrane reactors; Applied Catalysis; A: General 325; 2007; pp. 198-204.
Akin et al; Selective oxidation of ethane to ethylene in a dense tubular membrane reactor; Jr. Membr. Sci. 202; 2002; pp. 457-467.
Wang, et al; Continious oxygen ion transfer medium as a catalyst for high selective oxidative dehydrogenation of ethane; Cat. Ltrs.; Nov. 2002, vol. 84; Nos. 1-2; pp. 101-106.
Rebeilleau-Dassonneville et al.; Oxidative activation of ethane on catalytic modified dense ionic oxygen conducting membranes; Catalysis Today ; 2005; 104; pp. 131-137.
Chalakov et al; Oxidative dehydrogenation of ethane in an electro-chemical packed-bed membrane reactor; Chem. Engin. Jr.; 2009; 145; pp. 385-392.
Ahchieva, et al, Oxidative dehydrogenation of ethane in a fludized bed membrane reactor; Applied Catalysis; A: General ; 2005; 296; pp. 176-185.
Coronas, et al; Use of a ceramic membrane reactor for oxidative dehydrogenation of ethane to ethylene and higher hydrocarbons; Ind. Eng. Chem. Res.; 1995; 34; pp. 4229-4234.

* cited by examiner

*Primary Examiner* — In Suk Bullock
*Assistant Examiner* — Philip Louie
(74) *Attorney, Agent, or Firm* — Kenneth H Johnson

(57) ABSTRACT

The present invention provides a continuous process for the oxidative dehydrogenation of ethane to ethylene using a mixed oxide catalyst supported onto a ceramic membrane by supplying an oxygen containing gas (air or pure oxygen) and pure ethane to the opposite sides of the membrane, so that the paraffin and the oxygen do not directly mix in the reactor.

8 Claims, No Drawings

MEMBRANE-SUPPORTED CATALYSTS AND THE PROCESS OF OXIDATIVE DEHYDROGENATION OF ETHANE USING THE SAME

FIELD OF THE INVENTION

The present invention relates to the oxidative dehydrogenation of paraffins and particularly ethane to corresponding olefins. More particularly the present invention relates to a continuous process for the oxidative dehydrogenation of ethane wherein the catalyst comprises a ceramic membrane capable of separating the flows of oxygen-containing gas (air or pure oxygen) and pure ethane with a mixed oxide catalyst containing such active metal ions as vanadium, molybdenum, niobium, tellurium, and antimony taken in the right proportion and supported onto one of the surfaces of the membrane.

BACKGROUND OF THE INVENTION

Currently paraffins, particularly aliphatic paraffins, are converted to olefins using thermal cracking technology. The thermal cracking of paraffins to olefins, particularly lower paraffins such as $C_{2-4}$ paraffins typically ethane and propane to corresponding olefins is an energy intensive process. Typically the paraffins are passed through a furnace tube heated to at least 800° C., typically from about 850° C. to the upper working temperature of the alloy for the furnace tube, generally about 950° C. to 1000° C., for a period of time in the order of milliseconds to a few seconds. The paraffin molecule loses hydrogen and one or more unsaturated bonds are formed to produce an olefin. The current thermal cracking processes are not only cost intensive to build and operate but also energy intensive due to the substantial heat requirement for the endothermic cracking reactions which also results in greenhouse gas emissions. As a result, significant amounts of $CO_2$ are produced from the operation of these cracking furnaces.

Dehydrogenation processes are widely used in modern refining and petrochemistry. Processes for the synthesis of butadiene, isoprene, and long-chain olefins are commercialized. However, the area of dehydrogenation of light alkanes remains to be underexplored and especially ethane dehydrogenation is far from the commercial scale. The most advanced are the processes of oxidative dehydrogenation based on the use of transition metal oxide catalysts and a robust oxidant, such as oxygen or air. The oxidative conversion makes the process of dehydrogenation thermodynamically advantageous and may decrease the reaction temperature as compared to non-oxidative processes (e.g. thermal cracking). The conversion of ethane, which is the second major component of natural gas, to ethylene requires development of new processes.

However, the technology of oxidative dehydrogenation of ethane has not been commercially practiced for a number of reasons including the potential for an explosive mixture of oxygen and paraffin at an elevated temperature. For satisfactory conversion of paraffins to olefins, the required oxygen in the feed mixture should be typically higher than the maximum allowable level before entering the explosion range. Another reason is the requirement of either front end oxygen separation (from air) or a back end nitrogen separation, which often brings the overall process economy into the negative territory. Therefore, solutions to address these issues are being sorted in various directions.

In the current prior art when a mixed feed of oxygen and hydrocarbon is used care must be taken so that the amount of oxygen in the mixture does not exceed about 25 Vol. % or the mixed feed will exceed an explosive limit. As far as applicants have been able to determine only a few patents related to the prior art in this field, it was suggested to use ethane oxidative dehydrogenation mixed oxide catalysts supported onto one side of the ceramic membrane as an important component of the ethane oxidative dehydrogenation process that allows one to segregate the hydrocarbon feed from the oxygen containing feed to minimize the potential for a mixture of oxygen and hydrocarbon to occur or if such mixture occurs to approach the explosive limit.

Several catalytic systems are known in the art for the oxidative dehydrogenation of ethane. U.S. Pat. No. 4,450,313, issued May 22, 1984 to Eastman et al., assigned to Phillips Petroleum Company discloses a catalyst of the composition $LiO$—$TiO_2$, which is characterized by a low ethane conversion not exceeding 10%, in spite of a rather high selectivity to ethylene (92%). The major drawback of this catalyst is the high temperature of the process of oxidative dehydrogenation, which is close to or higher than 650° C.

The U.S. Pat. No. 6,624,116, issued Sep. 23, 2003 to Bharadwaj et al. and U.S. Pat. No. 6,566,573 issued May 20, 2003 to Bharadwaj et al., both assigned to Dow Global Technologies Inc., disclose Pt—Sn—Sb—Cu—Ag monolith systems that have been tested in an autothermal regime at T>750° C., the starting gas mixture contained hydrogen ($H_2$:$O_2$=2:1, GHSV=180 000 $h^{-1}$). The catalyst composition is different from that of the present invention and the present invention does not contemplate the use of molecular hydrogen in the feed.

U.S. Pat. No. 4,524,236 issued Jun. 18, 1985 to McCain, assigned to Union Carbide Corporation and U.S. Pat. No. 4,899,003 issued Feb. 6, 1990 to Manyik et al., assigned to Union Carbide Chemicals and Plastics Company Inc. disclose mixed metal oxide catalysts of V—Mo—Nb—Sb. At 375-400° C. the ethane conversion reached 70% with the selectivity close to 71-73%. However, these parameters were achieved only at very low gas hourly space velocities less than 900 $h^{-1}$ (i.e. 720 $h^{-1}$).

Rather promising results were obtained for nickel-containing catalysts disclosed in U.S. Pat. No. 6,891,075 issued May 10, 2005 to Liu, assigned to Symyx Technologies Inc. At 325° C. the ethane conversion on the best catalyst (a Ni—Nb—Ta oxide catalyst) in this series was about 20% with a selectivity of 85%. The patent teaches a catalyst for the oxidative dehydrogenation of a paraffin (alkane) such as ethane. The gaseous feedstock comprises at least the alkane and oxygen, but may also include diluents (such as argon, nitrogen, etc.) or other components (such as water or carbon dioxide). The dehydrogenation catalyst comprises at least about 2 weight % of NiO and a broad range of other elements preferably Nb, Ta, and Co. While NiO is present in the catalyst it does not appear to be the source of the oxygen for the oxidative dehydrogenation of the alkane (ethane).

U.S. Pat. No. 6,521,808 issued Feb. 18, 2003 to Ozkan et al., assigned to the Ohio State University, teaches sol gel supported catalysts for the oxidative dehydrogenation of ethane to ethylene. The catalyst appears to be a mixed metal system such as Ni—Co—Mo, V—Nb—Mo possibly doped with small amounts of Li, Na, K, Rb and Cs on a mixed silica oxide/titanium oxide support. Again the catalyst does not provide the oxygen for the oxidative dehydrogenation rather gaseous oxygen is included in the feed.

U.S. Pat. No. 7,319,179 issued Jan. 15, 2008 to Lopez-Nieto et al., assigned to Consejo Superior de Investigaciones Cientificas and Universidad Politecnica de Valencia, discloses Mo—V—Te—Nb—O oxide catalysts that provided an ethane conversion of 50-70% and selectivity to ethylene up to 95% (at 38% conversion) at 360-400° C. The catalysts have the empirical formula MoTe$_h$V$_i$Nb$_j$A$_k$O$_x$, where A is a fifth modifying element. The catalyst is a calcined mixed oxide (at least of Mo, Te, V and Nb), optionally supported on: (i) silica, alumina and/or titania, preferably silica at 20-70 wt % of the total supported catalyst or (ii) silicon carbide. The supported catalyst is prepared by conventional methods of precipitation from solutions, drying the precipitate then calcining.

Similar catalysts have been also described in open publications of Lopez-Nieto and co-authors. Selective oxidation of short-chain alkanes over hydrothermally prepared MoVTeNbO catalysts is discussed by F. Ivars, P. Botella, A. Dejoz, J. M. Lopez-Nieto, P. Concepcion, and M. I. Vazquez, in Topics in Catalysis (2006), 38 (1-3), 59-67.

MoVTe—Nb oxide catalysts have been prepared by a hydrothermal method and tested in the selective oxidation of propane to acrylic acid and in the oxidative dehydrogenation of ethane to ethylene. The influence of the concentration of oxalate anions in the hydrothermal gel has been studied for two series of catalysts, Nb-free and Nb-containing, respectively. Results show that the development of an active and selective active orthorhombic phase (Te$_2$M$_{20}$O$_{57}$, M=Mo, V, Nb) requires an oxalate/Mo molar ratio of 0.4-0.6 in the synthesis gel in both types of samples. The presence of Nb favors a higher catalytic activity in both ethane and propane oxidation and a better production of acrylic acid.

Mixed metal oxide supported catalyst compositions, catalyst manufacture and use in ethane oxidation are described in Patent WO 2005018804 A1, 3 Mar., 2005, assigned to BP Chemicals Limited, UK. A catalyst composition for the oxidation of ethane to ethylene and acetic acid comprises (i) a support and (ii) in combination with O, the elements Mo, V and Nb, optionally W and a component Z, which is metals of Group 14. Thus, Mo$_{60.5}$V$_{32}$Nb$_{7.5}$O$_x$ on silica was modified with 0.33 g-atom ratio Sn for ethane oxidation with good ethylene/acetic acid selectivity and product ratio 1:1.

A process for preparation of ethylene from gaseous feed comprising ethane and oxygen involving contacting the feed with a mixed oxide catalyst containing vanadium, molybdenum, tantalum and tellurium in a reactor to form an effluent of ethylene is disclosed in WO 2006130288 A1, 7 Dec., 2006, assigned to Celanese Int. Corp. The catalyst has a selectivity for ethylene of 50-80% thereby allowing oxidation of ethane to produce ethylene and acetic acid with high selectivity. The catalyst has the formula Mo$_1$V$_{0.3}$Ta$_{0.1}$Te$_{0.3}$O$_z$. The catalyst is optionally supported on a support selected from porous silicon dioxide, fused silica, kieselguhr, silica gel, porous and nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride, silicon carbide, and glass, carbon, carbon-fiber, activated carbon, metal-oxide or metal networks and corresponding monoliths; or is encapsulated in a material (preferably silicon dioxide (SiO$_2$), phosphorus pentoxide (P$_2$O$_5$), magnesium oxide (MgO), chromium trioxide (Cr$_2$O$_3$), titanium oxide (TiO$_2$), zirconium oxide (ZrO$_2$) or alumina (Al$_2$O$_3$).

The preparation of a supported catalyst usable for low temperature oxy-dehydrogenation of ethane to ethylene is disclosed in the U.S. Pat. No. 4,596,787 A, 24 Jun., 1986 assigned to UNION CARBIDE CORP. A supported catalyst for the low temperature gas phase oxydehydrogenation of ethane to ethylene is prepared by (a) preparing a precursor solution having soluble and insoluble portions of metal compounds; (b) separating the soluble portion; (c) impregnating a catalyst support with the soluble portion and (d) activating the impregnated support to obtain the catalyst. The calcined catalyst has the composition Mo$_a$V$_b$Nb$_c$Sb$_d$X$_e$. X is nothing or Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, Mn and/or W; a is 0.5-0.9, b is 0.1-0.4, c is 0.001-0.2, d is 0.001-0.1, e is 0.001-0.1 when X is an element.

Other examples of the low temperature oxy-dehydrogenation of ethane to ethylene using a calcined oxide catalyst containing molybdenum, vanadium, niobium and antimony are described in the U.S. Pat. No. 4,524,236 A, 18 Jun., 1985 and 4,250,346 A, 10 Feb., 1981, both assigned to UNION CARBIDE CORP. The calcined catalyst contains Mo$_a$V$_b$N-b$_c$Sb$_d$X$_e$ in the form of oxides. The catalyst is prepared from a solution of soluble compounds and/or complexes and/or compounds of each of the metals. The dried catalyst is calcined by heating at 220-550° C. in air or oxygen. The catalyst precursor solutions may be supported on to a support, e.g. silica, aluminium oxide, silicon carbide, zirconia, titania or mixtures of these. The selectivity to ethylene may be greater than 65% for a 50% conversion of ethane.

The application of dense ionic oxygen conducting membrane reactors (IOCMR), where both separation and reaction are integrated in a same unit is described in the papers by J.-A. Dalmon et al./Applied Catalysis A: General 325 (2007) 198-204; F. Akin, Y. Lin, J. Membr. Sci. 209 (2002); H. Wang, Y. Cong, W. Yang, Catal. Lett. 84 (2002) 101; M. Rebeilleau-Dassonneville et al. Catalysis Today 104 (2005) 131-137. However, the mechanism of the reaction involves the dissociation of oxygen, migration of O$^{2-}$ species and backward electron transfer through the dense ionic membrane and further oxidation of ethane producing ethylene. Although the ethane conversion on V/MgO/membrane or Pd/membrane catalysts reached about 100% at 1150K, the selectivity drops from 95% at 950K, when the reaction started to 60% at 1150K, and the total feed to the reaction side of the membrane was as low as 37 ml/min at P(ethane)/P(O2) ~0.255, so the overall oxidation process was very slow and had a negligible productivity. Also the reaction temperatures were extremely high (950-1150 K).

The authors (D. Farrusseng) describe the preparation of such ionic conducting membranes for the oxidative dehydrogenation of alkanes in WO2006/024785A1, Mar. 9, 2006.

A similar ionic membrane reactor for the catalytic oxidation of alkanes was disclosed in U.S. Pat. No. 6,730,808 A1, May 4, 2004, assigned to BASF. However, the only example given in the patent describes the oxidation of butane into maleic anhydride.

A model was developed for the electrochemical oxidative dehydrogenation of ethane to ethylene in a solid electrolyte membrane reactor (L. Chalakov, Chemical Engineering Journal 145 (2009) 385-392, but the process occurs at T~600° C., and the selectivity is lower than 50%.

Fluidized bed membrane reactor (FLBMR) was disclosed for the catalytic oxidative dehydrogenation of ethane using a γ-alumina supported vanadium oxide catalyst (D. Ahchieva, Applied Catalysis A: General 296 (2005) 176-185). The maximum ethylene yield observed in this type of reactor was 37% and a favorable operation range with respect to the oxygen-hydrocarbon ratio was observed, which indicates a lower sensitivity against oscillations and disturbances in the reactant feed, corresponding to a higher safety of operation. However, the W/F (mass of catalyst per unit volumetric gas flow rate) ratio was too high—between 150 and 230 kg/m$^3$, the selectivity to ethylene was below 70% and significant amounts of CO and CO2 were found in the products. Also, the reaction temperature was too high for the commercial realization (~600° C.).

A membrane catalytic reactor has been tested for the oxidative dehydrogenation of ethane (J. Coronas, Ind. Eng. Chem. Res. 1995, 34, 4229-4234). This reactor consists of a fixed bed of Li/MgO catalyst encompassed by a porous ceramic membrane. Oxygen was permeated through the membrane while ethane was fed axially. Two different configurations of the membrane reactor were tested: a homogeneous wall membrane reactor and a mixed system which was equivalent to a membrane reactor followed by a conventional fixed bed reactor. Using this system, high conversions of ethane were obtained, while maintaining a good selectivity. This gave yields to ethylene and higher hydrocarbons of up to 57%. In addition, the membrane reactor allowed a safe and stable operation, even when a relatively high proportion of oxygen was used in the overall feed. The major drawback of this system was a high temperature of the process (650-750° C.) and substantial coke formation suppressing the stability and life time of the catalyst.

Thus, none of the above art teaches or suggests the use of a continuous process of oxidative dehydrogenation of ethane using a mixed oxide catalyst containing vanadium, molybdenum, niobium, tellurium, and antimony supported onto one surface of the porous ceramic membrane in which oxygen and gaseous paraffin feeds are supplied separately to opposite sides of the membrane.

SUMMARY OF THE INVENTION

The present invention provides a process for the oxidative dehydrogenation of one or more $C_{2-6}$ alkanes (paraffins), preferably ethane or propane, to a corresponding olefin comprising continuous supplying of an oxygen containing gas and said paraffin to the opposite sides of a ceramic membrane with a catalytic oxidative dehydrogenation catalyst comprising a mixed oxide catalyst containing vanadium, molybdenum, niobium, tellurium, and antimony supported on the surface of the porous ceramic membrane exposed to said paraffin; at a temperature from 300° C. to 550° C., a pressure from 0.5 to 100 psi (3.447 to 689.47 kPa) said catalytic oxidative dehydrogenation catalyst comprising at least one component capable of extracting oxygen from said oxygen containing gas while it passes through said catalyst and releasing oxygen to the oxidative dehydrogenation reaction while said hydrocarbon passes through said catalyst.

In a further embodiment the alkane has a purity of greater than 95%.

In a further embodiment the process has a productivity of not less than 1000 g of olefin per kg of catalyst per hour.

In a further embodiment the process has a selectivity of not less than 95% to produce olefins.

In a further embodiment the process has an hourly space velocity of alkane and oxygen-containing gas of not less than 900 $h^{-1}$.

In a further embodiment the oxygen containing gas is selected from the group consisting of oxygen, mixtures comprising from 100 to 21 vol. % of oxygen and from 0 to 79 vol. % of one or more inert gases In a further embodiment said ceramic membrane comprises a porous tube or disc of alumina, zirconia, titania or a mixture of thereof with pore sizes ranging from 10 nm to 1000 nm.

In a further embodiment said catalyst optionally further comprises a metal oxide mixture of vanadium, niobium, molybdenum, tellurium and/or antimony oxides.

In a further embodiment said catalyst is deposited from an aqueous slurry onto one of the surfaces of the said ceramic membrane by impregnation, wash-coating, co-precipitation, brushing or spraying to provide from 1 to 10 weight % of said catalyst and from 99 to 90 weight % of said membrane.

In a further embodiment said catalyst comprises one or more catalysts selected from the group consisting of mixed oxide catalysts of the formula $V_xMo_yNb_zTe_mMe_nO_p$, wherein Me is a metal selected from the group consisting of Ti, Ta, Sb, Hf, W, Y, Zn, Zr, La, Ce, Pr, Nd, Sm, Sn, Bi, Pb Cr, Mn, Fe, Co, Cu, Ru, Rh, Pd, Pt, Ag, Cd, Os, Ir, Au, and mixtures thereof; and x is from 0.1 to 0.9;
y is from 0.001 to 0.5;
z is from 0.001 to 0.5;
m is from 0.001 to 0.5;
n is from 0.001 to 0.5; and
p is a number to satisfy the valence state of the mixed oxide catalyst.

In a further embodiment the space-time yield of olefin is not less than 1500 g/h per kg of catalyst.

In a further embodiment the catalyst has the formula $V_xMo_yNb_zTe_mMe_nO_p$, wherein Me is a metal selected from the group consisting of Ti, Ta, Sb, Hf, W, Y, Zn, Zr, La, Ce, Pr, Nd, Sm, Sn, Bi, Pb Cr, Mn, Fe, Co, Cu, Ru, Rh, Pd, Pt, Ag, Cd, Os, Ir, Au, and mixtures thereof; and:

x is from 0.2 to 0.5;
y is from 0.1 to 0.45;
z is from 0.1 to 0.45;
m is from 0.1 to 0.45;
n is from 0.01 to 0.45; and
p is a number to satisfy the valence state of the mixed oxide catalyst.

The foregoing embodiments may be combined in whole or part without deviating from the present invention or making a new invention.

DETAILED DESCRIPTION

The catalyst useful in accordance with the present invention may be any catalyst suitable for the oxidative dehydrogenation of one or more paraffins, preferably ethane or propane, to corresponding olefins, preferably alpha olefins. In one embodiment the catalyst itself is capable of taking oxygen from the oxygen containing gas and using the oxygen in the oxidative dehydrogenation of the paraffin.

The catalyst may comprise one or more catalysts selected from the group consisting of a mixed oxide catalyst of the formula $V_xMo_yNb_zTe_mMe_nO_p$, wherein Me is a metal selected from the group consisting of Ti, Ta, Sb, Hf, W, Y, Zn, Zr, La, Ce, Pr, Nd, Sm, Sn, Bi, Pb Cr, Mn, Fe, Co, Cu, Ru, Rh, Pd, Pt, Ag, Cd, Os, Ir, Au, and mixtures thereof; and x is from 0.1 to 0.9, preferably from 0.2 to 0.5;
y is from 0.001 to 0.5, preferably from 0.1 to 0.45;
z is from 0.001 to 0.5, preferably from 0.1 to 0.45;
m is from 0.001 to 0.5, preferably from 0.1 to 0.45;
n is from 0.001 to 0.5, preferably from 0.01 to 0.45; and
p is a number to satisfy the valence state of the mixed oxide catalyst.

In a further embodiment in the catalyst the ratio of x:m is from 0.3 to 10, most preferably from 0.5 to 8, desirably from 0.5 to 6.

The methods of preparing the catalysts are known to those skilled in the art. For example, the catalyst may be prepared by mixing aqueous solutions of soluble metal compounds such as hydroxides, sulphates, nitrates, halides lower ($C_{1-5}$) mono or di carboxylic acids and ammonium salts or the metal acid per se. For instance, the catalyst could be prepared by blending solutions such as ammonium metavanadate, niobium oxalate, ammonium molybdate, telluric acid etc. The resulting solution is then dried typically in air at 100-150° C. and calcined in a flow of inert gas such as those selected from the group consisting of $N_2$, He, Ar, Ne and mixtures thereof at 200-600° C., preferably at 300-500° C. The calcining step may take from 1 to 20, typically from 5 to 15 usually about 10 hours. The resulting oxide is a friable solid typically insoluble in water.

Typically the catalyst is supported onto one surface of the porous ceramic membrane by any appropriate method. For example the catalyst could be deposited from an aqueous slurry onto one of the surfaces of the said ceramic membrane by impregnation, wash-coating, brushing or spraying to provide from 1 to 10 weight % of said catalyst and from 99 to 90 weight % of said membrane. The catalyst could also be co-precipitated from a slurry with the ceramic precursor (e.g. alumina). In the supported catalyst, the catalyst may be present in an amount from 0.1 to 20 preferably 1 to 10, most preferably from 2 to 5 weight % of the supported catalyst and the membrane is present in an amount from 99.9 to 80 preferably from 99 to 90, most preferably from 98 to 95 weight % of the total membrane catalyst.

The porous ceramic membrane for supporting the catalyst may be formed from oxides, dioxides, nitrides, carbides and phosphates selected from the group consisting of porous silicon dioxide, fused silicon dioxide, porous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, yttrium oxide, aluminum silicate, silicon nitride, silicon carbide and mixtures thereof.

Preferred components for forming ceramic membranes include oxides of titanium, zirconium, aluminum, magnesium, silicon and mixtures thereof.

The ceramic membrane may be prepared from the ceramic material using conventional techniques. For example the starting material may be cleaned, washed and dried (or spray dried) or produced from a sol/gel of the ceramic and where necessary ground or milled to the appropriate particle size (typically from 10 microns up to about a half a millimeter). The powder may be subjected to benefication such as acid or base washing to alter the pore size of the ceramic.

The resulting powder is dried or calcined to remove associated water (water of hydration etc.) and may be formed into a suitable ceramic substrate such as a disk or a tube by for example compression molding or isostatic compaction at pressures from about 5 to 200 MPa ($1-29 \times 10^6$ psi), with or without a binder and sintering at temperatures to fuse the particles. (e.g. at temperatures from about 0.5 to 0.75 of the melting temperature of the ceramic material.

Other techniques may be used such as tape casting or slip casting of slurries and the subsequent "punching of" the required shape such as circular, square etc.

The ceramic membrane may have a thickness from about 1 to 10 mm, typically from 2 to 8 mm, preferably from 3 to 7 mm.

The porous ceramic membrane may have a broad range of surface area, typically greater than 1 $m^2/g$ up to 1,000 $m^2/g$. High surface area membranes may have a surface area greater than 250 $m^2/g$ (e.g. from 250 to 1,000 $m^2/g$). Low to moderate surface area supports may have a surface area from 1 to 250 $m^2/g$, preferably from about 10 to 200 $m^2/g$. It is believed the higher surface area membranes will produce more $CO_2$ during the oxidative dehydrogenation of the alkane (paraffin).

The membrane will be porous and may have a pore volume up to about 2.0 ml/g, preferably less than 1 ml/g, preferably from about 0.1 to 0.5 ml/g.

Other than for co-precipitation it is important that the membrane be dried prior to supporting the oxide catalyst. Generally, the membrane may be heated at a temperature of at least 200° C. for up to 24 hours, typically at a temperature from 500° C. to 800° C. for about 2 to 20 hours, preferably 4 to 10 hours. The resulting membrane will be free of adsorbed water and should have a surface hydroxyl content from about 0.1 to 5 mmol/g, preferably from 0.5 to 3 mmol/g.

There are number of methods which may be used to deposit the catalyst onto the surface of the ceramic membrane. The membrane could simply be impregnated with a suspension of the calcined catalyst. The catalyst would be suspended in a solvent or diluent inert to the catalyst. The membrane would then be impregnated with the suspension and dried, typically under an inert gas or in air.

The catalyst could also be supported onto one side of the membrane by impregnation/filtration of the catalyst suspension upon continuous evacuation from the other side of the membrane to provide formation of a more dense and uniform catalytic layer. Preferable catalyst particle size in suspension can be related in this case with membrane pore sizes (1-800 nm). The catalyst can be also provided by co-precipitation of the oxide phases from the appropriate precursors from aqueous solutions.

The catalyst could also be supported onto the surface of the membrane by spraying of the suspension in an appropriate solvent and further drying. The catalyst could also be supported onto the surface of the membrane by wash coating from the suspension in an appropriate solvent and further drying.

The feed to the reactor comprises two separate flows to opposite sides of the membrane. One flow, to the ceramic surface without the oxidative dehydrogenation catalyst, is an oxygen containing gas which is selected from the group consisting of oxygen, mixtures comprising from 100 to 21 vol. % of oxygen and from 0 to 79 vol. % of one or more inert gases. Some inert gases may be selected from the group consisting of nitrogen, helium and argon and mixtures thereof. Preferably the oxygen containing gas is air as it provides for a much simpler plant operation.

The second flow, to the side of the ceramic membrane supporting the oxidative dehydrogenation catalyst, comprises one or more, preferably a $C_2$-$C_6$, preferably $C_2$-$C_4$ paraffin, most preferably ethane or an ethane containing gas which is selected from the group consisting of pure (undiluted) ethane, mixtures comprising from 5 to 95 wt % of ethane and from 95 to 5 weight % of one or more gases selected from the group consisting of methane, nitrogen, helium and argon and mixtures thereof. Preferably the ethane containing gas is undiluted ethane as it provides for a much simpler plant operation and better productivity (space-time yield).

The paraffin, typically ethane, should have a purity greater than 90%, preferably greater than 95%, most preferably greater than 98%.

The ratios of the gas components will be a function of the method of operating the reaction to reach either the complete consumption of oxygen, or complete consumption of ethane, or both. The further separation will include separation of ethylene from unreacted ethane or admixed gases (methane, $CO_2$, inert gases, oxygen). The oxygen containing gas flow rate has to be large enough to provide sufficient oxygen to the catalyst to provide the oxygen needed for the oxidative dehydrogenation reaction when the hydrocarbon stream passes over the oxidative dehydrogenation catalyst optionally containing one or more metal oxides. The rate of oxygen gas should be sufficient to keep catalyst active but low enough to minimize carryover of oxygen into product gas (olefin). One can calculate the ratio of oxygen to paraffin based on the stoichiometry of the reaction. However, the reaction will also be affected by the take up and release rate of the oxygen to and from the catalyst, because oxygen is fed to the opposite side of the membrane and is supplied to the active mixed oxide catalyst through the porous ceramic membrane. The rate of oxygen supply is regulated by the extra-pressure ($\Delta P$) from the oxygen side of the membrane varying typically from 0.05 to 0.5 atm. Typically the molar ratio of hydrocarbon (paraffin) to oxygen feed may range from 1:1 to 3:1, preferably from 1.5:1 to 2.5:1. Given the foregoing one of ordinary skill in the art will be able to determine the preferred ratio and flow rates of the two gas flows. The shut down of the oxygen flow results in fast but reversible loss of the ethane conversion.

The oxidative dehydrogenation may be conducted at temperatures from 300° C. to 550° C., typically from 300° C. to 500° C., preferably from 350° C. to 450° C., at pressures from 0.5 to 100 psi (3.447 to 689.47 kPa), preferably from 15 to 50 psi (103.4 to 344.73 kPa), and the residence time of the paraffin in the reactor is typically from 0.5 to 30 seconds preferably from 1 to 10 seconds. The ethane feed should be of purity of preferably 95%, most preferably 98%. Preferably the process has a selectivity for olefin (ethylene) of greater than 95%, preferably greater than 98%. The gas hourly space velocity (GHSV) will be from 500 to 30000 $h^{-1}$, preferably greater than 1000 $h^{-1}$. The space-time yield of ethylene (productivity) in g/hour per Kg of the catalyst should be not less than 900, preferably greater than 1500, most preferably greater than 3000, most desirably greater than 3500 at 350-400° C. It should be noted that the productivity of the catalyst will increase with increasing temperature.

The reactor may be a flow reactor of ideal substitution.

The present invention will be demonstrated by the following non limiting examples.

EXAMPLES

Example 1

Preparation of the Active Oxide Catalyst Phase, No Membrane 2.65 g of ammonium heptamolybdate (tetrahydrate) and 0.575 g of telluric acid were dissolved in 19.5 g of distilled water at 80° C. Ammonium hydroxide (25% aqueous solution) is added to the Mo- and Te-containing solution at a pH of 7.5. Then water is evaporated under stirring at 80° C. The solid precipitate is dried at 90° C. 3.0 g of this precipitate is suspended in water (21.3 g) at 80° C. and 0.9 g of vanadyl sulfate and 1.039 g of niobium oxalate were added. The mixture was stirred for 10 min and then is transferred to the autoclave with a Teflon® (tetrafluoroethylene) lining. Air in the autoclave was substituted with argon, the autoclave was pressurized and heated to 175° C. and the system was kept for 60 hours at this temperature. Then the solid formed in the autoclave was filtered, washed with distilled water and dried at 80° C. The thus obtained active catalyst phase was calcined at 600° C. (2 h) in a flow of argon. The temperature was ramped from room temperature to 600° C. at 1.67° C./min. The powder was pressed then and the required mesh size particles were collected.

Catalyst Activity

The catalyst was tested in oxidative dehydrogenation of ethane using a gas mixture $O_2/C_2H_6$ with an $O_2$ content of 25% (outside the explosive limit). The mixture was fed in the plug-flow reactor with the gas hourly space velocity of 900 $h^{-1}$ at a pressure of 1 atm.

The catalyst was tested at 420° C., the catalyst loading 0.13-1.3 g; fraction 0.25-0.5 mm, a flow type reactor with a stationary catalyst bed was used. The catalyst was heated to 360° C. in the reaction mixture and the catalytic activity was measured at 400-450° C. The data for are presented in the Table 1 (Entry 1).

Example 2

The catalyst (780 mg) of Example 1 was supported by wash coating using an aqueous suspension of catalyst of Example 1 or co-precipitation of the components of the oxide catalyst onto an alumina ceramic membrane (tube od 7.5 mm, id 5 mm, length 125 mm) and the membrane with the supported catalyst was tested in the same reactor used in Example 1 in oxidative dehydrogenation of ethane under conditions of separate down-flow supply of pure ethane from the side of the membrane coated with the catalyst and pure oxygen supply from the other side of the membrane (uncoated). The results at the ethane:O2 ratio of 2:1 and overall space velocity (VHSV) of 900 $h^{-1}$ are presented in Table 1 (Entry 2).

TABLE 1

| Example | Temperature, ° C. | Conversion of $C_2H_6$, % | Conversion of $O_2$, % | Space-time yield of ethylene (productivity) g/hr per 1 kg of catalyst | Selectivity to ethylene % |
|---|---|---|---|---|---|
| 1 (bulk) | 400 | 20 | 30 | 150 | 92 |
|  | 450 | 35 | 70 | 240 | 90 |
| 2 (membrane-supported catalyst) | 400 | 40 | 60 | 1400 | 98 |
|  | 450 | 60 | 90 | 2240 | 95 |

It is seen from this comparison that the process of the invention based on the use of a mixed oxide catalyst supported onto the porous ceramic membrane provides at least 5-10 times higher productivity of the same catalyst in the oxidative dehydrogenation of ethane as compared to the bulk catalyst tested in the plug-flow reactor. The use of pure ethane and pure oxygen contributes to the higher space velocity. Also the selectivity remains high, >95%, without a clear dependence on the space velocity of the gas flows of ethane and oxygen. The process is safe, as explosive limits are not approached, and energy and resource efficient.

What is claimed is:

1. A process for the oxidative dehydrogenation of a $C_{2-6}$ alkane having a purity of greater than 95% to the corresponding olefins at a selectivity of not less than 95% of said corresponding olefin comprising:

continuously supplying an oxygen containing gas and said alkane to the opposite sides of an inert porous ceramic membrane with a catalytic dehydrogenation catalyst supported on the surface of the porous ceramic membrane exposed to said alkane at a temperature from 300° C. to 550° C., a pressure from 0.5 to 100 psi (3.447 to 689.47 KPa), a productivity of not less than 1000 g of olefin per kg of catalyst per hour and an hourly space velocity of alkane and oxygen containing gas of not less than 900 $h^{-1}$, wherein the oxidative dehydrogenation catalyst is supported on inert porous ceramic membrane having a surface area from 10 to 200 $m^2/g$, a pore volume from 0.1 to 0.5 ml/g and is selected from the group consisting of oxides of titanium, zirconium, aluminum, silicon and mixture thereof, to provide from 1 to 20 weight % of said catalyst and from 99 to 80 weight % of said porous membrane;

and wherein said catalytic dehydrogenation catalyst comprises a mixed oxide catalyst selected from the group consisting of mixed oxide catalysts of the formula $V_xMo_yNb_zTe_mMe_nO_p$, wherein Me is a metal selected from the group consisting of Ti, Ta, Sb, Hf, W, Y, Zn, La, Ce, Pr, Nd, Sm, Sn, Bi, Pb, Cr, Mn, Fe, Co, Cu, Ru, Rh, Pd, Pt, Ag, Cd, Os, Ir, Au, and mixture thereof; and x is from 0.1 to 0.9;
y is from 0.001 to 0.5;
z is from 0.001 to 0.5;
m is from 0.001 to 0.5;
n is from 0.001 to 0.5;
p is a number to satisfy the valence state of the mixed oxide catalyst; the ratio of x:m is from 0.5 to 8; and wherein said catalytic oxidative dehydrogenation catalyst also comprises at least one component capable of extracting oxygen from said oxygen containing gas while it passes through said catalyst and releasing oxygen to the oxidative dehydrogenation reaction while said alkane passes through said catalyst to prevent the formation of an explosive mixture of said alkane and said oxygen containing gas.

2. The process according to claim 1, wherein the oxygen containing gas is selected from the group consisting of oxygen and mixtures comprising from 100 to 21 vol. % of oxygen and from 0 to 79 vol. % of one or more inert gases.

3. The process according to claim 2, wherein the catalyst is supported by impregnation of the porous ceramic membrane with a suspension of fine powder of the said catalyst in an aqueous slurry.

4. The process according to claim 2, wherein the catalyst is supported by coating or co-precipitation of the components of the mixed oxide catalyst onto the porous ceramic membrane with a suspension of fine powder of the said catalyst in water.

5. The process according to claim 2, wherein the catalyst is supported by brushing of the porous ceramic membrane with a suspension of fine powder of the said catalyst in water.

6. The process according to claim 2, wherein the catalyst is supported by spraying of the porous ceramic membrane with a suspension of fine powder of the said catalyst in water.

7. The process according to claim 2, wherein the space-time yield of ethylene is not less than 1500 g/h per kg of catalyst.

8. The process according to claim 2, wherein the catalyst has the formula $V_xMo_yNb_zTe_mMe_nO_p$, wherein Me is a metal selected from the group consisting of Ti, Ta, Sb, Hf, W, Y, Zn, La, Ce, Pr, Nd, Sm, Sn, Bi, Pb, Cr, Mn, Fe, Co, Cu, Ru, Rh, Pd, Pt, Ag, Cd, Os, Ir, Au, and mixture thereof; and x is from 0.2 to 0.5;
y is from 0.1 to 0.45;
z is from 0.1 to 0.45;
m is from 0.1 to 0.45;
n is from 0.01 to 0.45;
and p is a number to satisfy the valence state of the mixed oxide catalyst.

* * * * *